United States Patent [19]

Pauling et al.

[11] Patent Number: 4,687,859

[45] Date of Patent: Aug. 18, 1987

[54] MONOESTERS OF IMIDAZOLIDINONE DICARBOXYLIC ACIDS

[75] Inventors: Horst Pauling, Bottmingen; Christof Wehrli, Birsfelden, both of Switzerland

[73] Assignee: Hoffmann-La Roche Inc., Nutley, N.J.

[21] Appl. No.: 734,307

[22] Filed: May 15, 1985

[30] Foreign Application Priority Data

May 18, 1984 [CH] Switzerland ............... 2458/84
Feb. 22, 1985 [CH] Switzerland ............... 825/85

[51] Int. Cl.$^4$ .................................... C07D 233/28
[52] U.S. Cl. .............................. 548/321; 548/303; 548/318
[58] Field of Search ................... 548/318, 321

[56] References Cited

U.S. PATENT DOCUMENTS 3,700,659 10/1972 Gerecke et al. .......... 548/321 X
4,403,096  9/1983 Hazama et al. .......... 548/321

FOREIGN PATENT DOCUMENTS 0092194 10/1983 European Pat. Off. ........ 548/321

Primary Examiner—Richard A. Schwartz
Attorney, Agent, or Firm—John S. Saxe; Bernard S. Leon; George W. Johnston

[57] ABSTRACT

A novel process for the manufacture of the optically active lactone of the formula

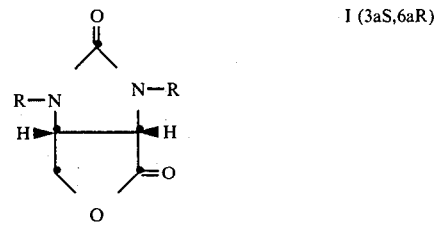

is described.

4 Claims, No Drawings

MONOESTERS OF IMIDAZOLIDINONE DICARBOXYLIC ACIDS

BACKGROUND OF THE INVENTION

The present invention is concerned with a novel process for the manufacture of the optically active lactone of the formula

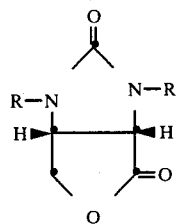

I (3aS,6aR)

wherein R represents the benzyl residue.

This optically active lactone of formula I is a known, valuable intermediate in the synthesis of (+)-biotin, as well as of derivatives thereof and compounds related thereto.

Under the expression "(3aS,6aR)" in connection with formula I there is to be understood in the scope of the present invention that antipode which is dextrorotatory in benzene or chloroform. This antipode is referred to hereinafter as the (+)-lactone.

Processes for the manufacture of the (+)-lactone of formula I are already known from German Patent Specification No. 2058248 (corresponding to U.S. Pat. No. 3,700,659) and from European Patent Publication No. 44 158 (corresponding to U.S. Pat. No. 4,403,096). In the first case, racemic half esters are resolved into their optical antipodes and the desired antipode is converted into the (+)-lactone of formula I. In the second case, a dicarboxylic acid or the corresponding anhydride is reacted with a particular optically active amine, whereby the (S)-amic acid is formed in excess. This can subsequently, after esterification of the carboxyl group, be reduced with sodium borohydride and hydrolyzed to the desired (30 )-lactone of formula I. Both processes have disadvantages, in that on the one hand a racemate resolution must be carried out with recyclization of the undesired antipode and on the other hand in order to obtain a good yield the likewise formed (R)-amic acid as well as other byproducts must also be recyclized. Moreover, in the latter case the carboxyl group which is still free after the amide formation must be esterified in order to permit the required reduction to the (+)-lactone of formula I.

SUMMARY OF THE INVENTION

There accordingly exists a need for a process in accordance with which the (+)-lactone of formula I can be obtained in high yield, with large optical purity, without recyclization of undesired byproducts or without previous amide formation. This need has now been met in accordance with the invention. Thus, it has surprisingly been found that by reacting a cycloanhydride of the formula

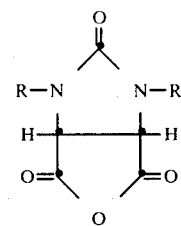

II wherein R is benzyl, with particular chiral alcohols, there is formed almost exclusively a desired half ester which can be converted readily by reduction into the (+)-lactone of formula I.

DETAILED DESCRIPTION OF THE INVENTION

The process in accordance with the invention for producing an optically active (+)-lactone of the formula

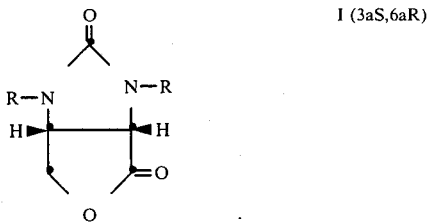

I (3aS,6aR)

wherein R is the benzyl residue, comprises reacting a cycloanhydride of the formula

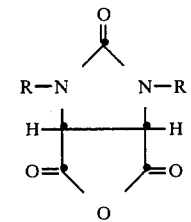

II wherein R has the above significance
with a secondary, chiral alcohol of the formula

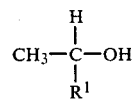

III wherein $R^1$ is a residue of the formula

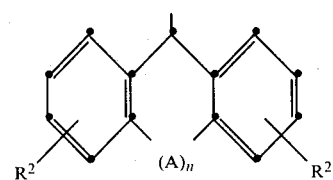

(a)

-continued

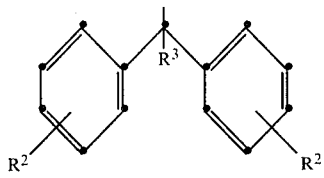

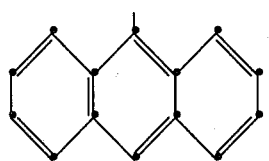

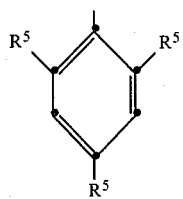

or

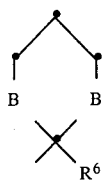

in which $R^2$ is hydrogen, halogen, lower alkyl or lower alkoxy; $R^3$ is hydrogen or hydroxy or, when $R^2$ in the residue (b) is hydrogen, $R^3$ also can be lower alkyl, lower alkoxy or phenyl; $R^4$ is cycloalkyl, thienyl, 2-furyl, or phenyl which phenyl is unsubstituted or substituted with chlorine or methyl; $R^5$ is hydrogen or lower alkyl; $R^6$ is lower alkyl or phenyl; A is sulphur or methylene; B is sulphur, —SO$_2$— or methylene; and n is the integer 1 when A is sulphur or n is the integer 1 or 2 when A is methylene,
and reducing the resulting half ester of the formula

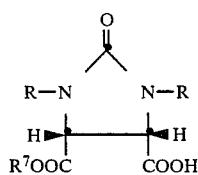    IV wherein $R^7$ is the residue

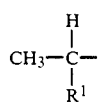

and R and $R^1$ have the above significance, with a complex borohydride thereby to form (+)-lactone of formula I.

The term "lower alkyl" signifies in the scope of the present invention straight-chain or branched alkyl groups with 1 to 5 carbon atoms such as methyl, ethyl, propyl, isopropyl, n-butyl, isobutyl, pentyl and the like. The term "lower alkoxy" signifies groups in which the alkyl residue has the foregoing significance. The term "halogen" signifies fluorine, chlorine or bromine. The term "cycloalkyl" signifies groups with 3 to 7 carbon atoms such as cyclopropyl, cyclobutyl, cyclopentyl, cyclohexyl and cycloheptyl.

The term "alkali metal" denotes sodium, potassium or lithium.

Under "complex borohydrides" there are to be understood in the scope of the present invention especially those in which the cation can be an alkali metal such as lithium, sodium or potassium or a tetraalkylammonium ion such as tetrabutylammonium. Lithium borohydride is especially preferred.

Some of the chiral alcohols of formula III which are used are known compounds and some are novel compounds and can be prepared in a manner known per se from known compounds. However, in this case care must be taken that the chiral alcohols obtained are always enantiomerically uniform. Preferred alcohols of formula III are those in which $R^1$ represents a residue of formula (d).

The reaction of the cycloanhydride of formula II with a chiral, secondary alcohol of formula III can be carried out in a manner known per se. The reaction is conveniently carried out under an inert gas such as, for example, carbon dioxide, argon, nitrogen and the like, and in an anhydrous, organic solvent which is inert under the reaction conditions. As solvents there can be named, in particular, aromatic hydrocarbons such as benzene, toluene, xylene, anisole, chlorobenzene and the like, ethers such as diethyl ether, tetrahydrofuran, dioxan or polyethers such as monoglyme or diglyme and the like, halogenated hydrocarbons such as methylene chloride, chloroform or also dimethylformamide, dimethyl sulphoxide, acetonitrile, cyclohexene, carbon disulphide etc. Preferred solvents are aromatic hydrocarbons and especially the previously mentioned.

The reaction can be carried out, preferably, in the presence of a catalyst. As such catalysts there come into consideration, for example, tertiary amines such as, for example, diazabicyclooctane, diazabicycloundecene, p-dimethylaminopyridine and the like as well as trialkylamines containing lower alkyl residues such as triethylamine etc. Where the reaction is carried out in the presence of a catalyst, the latter is conveniently used in stoichiometric amounts. Furthermore, the reaction can be carried out at a temperature of about −70° C. to the reflux temperature of the reaction mixture. The reaction is preferably carried out at a temperature of about −50° C. to about room temperature (about 23° C.) and especially at a temperature of about −30° C. to about 0° C. The pressure at which this reaction is carried out has no critical significance.

An especially preferred embodiment of the process in accordance with the invention comprises reacting the cycloanhydride of formula II with a [S]-1,1-diarylpropanol or [S]-1,1-diarylpropane-1,2-diol, preferably with [S]-1,1-diphenylpropanol or [S]-1,1-diphenyl-1,2-propanediol, in an aromatic hydrocarbon, especially toluene, at a temperature of −20° C. to 0° C. in the presence of stoichiometric amounts of catalyst, especially diazabicyclooctane.

The reduction of the half ester of formula IV can be carried out in situ or also after its isolation. The free carboxyl group is conveniently converted into a salt before carrying out the reduction if the reaction of the cycloanhydride of formula II with an alcohol of formula III has not been carried out in the presence of a catalyst. The reduction itself can be carried out by means of a complex borohydride, preferably by means of lithium borohydride. The reduction is conveniently carried out in an inert gas atmosphere, for example under nitrogen or argon, in an inert organic solvent such as an ether, for example dioxan or tetrahydrofuran or an ether of glycol or diethylene glycol, for diethylene glycol dimethyl ether, and at a temperature of about room temperature to the reflux temperature of the reaction mixture. The lithium borohydride which is preferably used in this case can be employed as such or can be formed in situ from sodium borohydride or potassium borohydride and lithium chloride or lithium bromide.

The following Examples serve to illustrate the invention and represent no limitation thereof whatsoever. Room temperature is about 23° C. Unless otherwise indicated, the Examples were carried out as written.

The optical purity "e.e." given in the Examples is based on a lactone of formula I with $[\alpha]_D^{20} = +62.0°$ (1% in CHCl$_3$).

EXAMPLE 1

(A) 1.01 g (3 mmol) of cis-1,3-dibenzyl-hexahydro-1H-furo[3,4-d]imidazole-2,4,6-trione in 10 ml of toluene and 0.637 g (3 mmol) of [S]-1,1-diphenyl-2-propanol ($[\alpha]_{365}^{20} = -218.6°$ (0.5% in ethanol)) are placed in an apparatus standing under argon. To this suspension there is added dropwise at $-10°$ C. within 30 minutes a solution of 0.168 g (1.5 mmol) of diazabicyclooctane in 10 ml of toluene. After 18 hours at $-10°$ C. the now clear solution is stirred at room temperature for a further 1 hour. It is then acidified with 30 ml of 0.1N HCl and extracted in 3 separating funnels with 100 ml of ether each time. The organic phases are washed three times with 30 ml of water each time, combined, dried over sodium sulphate and concentrated. There are obtained 2.8 g of 5-[-[S]-1,1-diphenyl-2-propyl]-4-hydrogen-cis-1,3-dibenzyl-2-oxo-4,5-imidazolidinedicarboxylate.

(B) 5.7 ml of a 1.05 molar lithium borohydride solution in tetrahydrofuran (6 mmol) are placed in an apparatus standing under argon. Thereto there is added dropwise within 1 hour at 40°-45° C. a solution of 2.8 g (3 mmol) of 5-[-[S]-1,1-diphenyl-2-propyl]-4-hydrogen-cis-1,3-dibenzyl-2-oxo-4,5-imidazolidinedicarboxylate (prepared in accordance with (A)) in 20 ml of tetrahydrofuran and 0.42 ml of triethylamine (3 mmol). The mixture is stirred at 40° C. for a further 2 hours and subsequently treated with 3.5 ml of 3N HCl. Thereupon, the reaction mixture is stirred at 70° C. for 30 minutes and extracted in 2 separating funnels with in each case 150 ml of ether. The organic phases are washed three times with 50 ml of water each time, combined, dried over sodium sulphate and concentrated. The residue (1.65 g) is chromatographed on 150 g of silica gel with 600 ml of n-hexane/ether (4:6, v/v) and subsequently with 800 ml of toluene/acetone/glacial acetic acid (92:5:3, v/v). There is obtained 0.772 g (80% of (3aS,6aR)-1,3-dibenzyl-dihydro-1H-furo[3,4-d]imidazole-2,4(3H,3aH)-dione.

$[\alpha]_D^{20} = +59.4°$ (1% in CHCl$_3$), which corresponds to an optical purity of 95.8% e.e. After recrystallization from 7.7 ml of isopropanol the product has a rotation of $[\alpha]_D^{20} = +61.3°$ (1% in CHCl$_3$), which corresponds to an optical purity of 98.7% e.e.

EXAMPLE 2

(A) 0.336 g (1 mmol) of cis-1,3-dibenzyl-hexahydro-1H-furo[3,4-d]imidazole-2,4,6-trione, 5 ml of tetrahydrofuran and 0.238 g (1 mmol) of (+)-10,11-dihydro-α-methyl-5H-dibenzo[a,d]cycloheptene-5-methanol ($[\alpha]_{365}^{20} = +326.8°$ (1% in ethanol)) are placed in an apparatus standing under argon. Thereto there is added dropwise within 30 minutes at room temperature a solution of 0.14 ml of triethylamine in 5 ml of tetrahydrofuran. The suspension dissolves during the dropwise addition. After 18 hours 10 ml of 1N HCl are added and the product is extracted twice with 100 ml of ether each time. The organic phases are washed three times with 20 ml of water each time, combined, dried over sodium sulphate and concentrated. There is obtained 0.50 g (87%) of 5-[1-(10,11-dihydro-5H-dibenzo[a,d]cyclohepten-5-yl)ethyl]-4-hydrogen-cis-1,3-dibenzyl-2-oxo-4,5-imidazolidinedicarboxylate.

(B) 5 ml of a 0.4 molar lithium borohydride solution in tetrahydrofuran (2 mmol) are placed in an apparatus standing under argon. To this solution there is added dropwise at 40° C. within 30 minutes a solution of 0.5 g (0.87 mmol) of 5-[1-(10,11-dihydro-5H-dibenzo[a,d]cyclohepten-5-yl)ethyl]-4-hydrogen-cis-1,3-dibenzyl-2-oxo-4,5-imidazolidinedicarboxylate (prepared in accordance with A), 10 ml of tetrahydrofuran and 0.12 ml (0.87 mmol) of triethylamine. The mixture is stirred at 40° C. for a further 2.5 hours. The solution is cooled to 10° C. and then decomposed with 5 ml of 3N HCl. The mixture is subsequently stirred at 60° C. for 30 minutes and the product is extracted twice with 100 ml of ether each time. The organic phases are washed three times with 20 ml of water each time, combined, dried over sodium sulphate and concentrated. The resulting 0.60 g of crude product is chromatographed on 150 g of silica gel. The chiral alcohol is eluted with 600 ml of cyclohexane/ether (6:4, v/v) and thereafter the (+)-lactone obtained is eluted with 800 ml of toluene/acetone/glacial acetic acid (92:5:3, v/v). There is obtained 0.229 g (82%) of (3aS,6aR)-1,3-dibenzyl-dihydro-1H-furo[3,4-d]imidazole-2,4(3H,3aH)-dione.

$[\alpha]_D^{20} = +52.7°$ (1% in CHCl$_3$), which corresponds to an optical purity of 85% e.e.

After the recrystallization of 0.2 g from 2 ml of isopropanol the product has a rotation of $[\alpha]_D^{20} = +59°$ (1% in CHCl$_3$), which corresponds to an optical purity of 95% e.e.

EXAMPLE 3

0.53 g (1.58 mmol) of cis-1,3-dibenzyl-hexahydro-1H-furo[3,4-d]imidazole-2,4,6-trione, 0.354 g (1.58 mmol) of (+)-9,10-dihydro-α-methyl-9-anthracene-methanol ($[\alpha]_{365}^{20} = +63.4°$ (1% in ethanol)) and 5 ml of tetrahydrofuran are placed in an apparatus standing under argon and there is added dropwise thereto within 30 minutes at room temperature a solution of 0.22 ml (1.58 mmol) of triethylamine in 5 ml of tetrahydrofuran. After 18 hours the clear solution is added dropwise at 40° C. within 30 minutes to 3 ml of a 1 molar lithium borohydride solution in tetrahydrofuran (3 mmol). After stirring at 40° C. for 2 hours the mixture is cooled to 10° C. and decomposed with 5 ml of 3N HCl. After stirring at room temperature for 24 hours the product is extracted twice with 100 ml of ether each time and washed three times with 20 ml of water each time. The organic phases are combined, dried over Na₂SO₄ and concentrated. The residue is chromatographed on 150 g of silica gel with 600 ml of cyclohexane/ether (6:4, v/v) and subsequently with 800 ml of toluene/acetone/glacial acetic acid (92:6:3, v/v). There are obtained 0.31 g of the alcohol used with $[\alpha]_{365}^{20} = +60.8°$ (1% in ethanol) and 0.404 g of (3aS,6aR)-1,3-dibenzyl-dihydro-1H-furo[3,4-d]imidazole-2,4(3H,3aH)-dione. $[\alpha]_D^{20} = +51.6°$ (1% in CHCl₃), which corresponds to an optical purity of 83.2% e.e.

After the recrystallization of 0.3 g from 3 ml of isopropanol the product has a rotation of $[\alpha]_D^{20} = +58.4°$ (1% in CHCl₃), which corresponds to an optical purity of 94.2% e.e.

EXAMPLE 4

0.336 g (1 mmol) of cis-1,3-dibenzyl-hexahydro-1H-furo[3,4-d]imidazole-2,4,6-trione in 3.3 ml of tetrahydrofuran are placed in an apparatus standing under argon. There is then added dropwise within 15 minutes at room temperature a solution of 0.15 ml (1.1 mmol) of triethylamine and 0.224 g (1 mmol) of [S]-1,1-di-(3-thienyl)-2-propanol ($[\alpha]_{365}^{20} = -77.4°$ (1% in ethanol)) in 3.3 ml of tetrahydrofuran. The solution is then stirred at room temperature for 1.5 hours. To this solution there are added at 40°–50° C. while gassing with argon 1.9 ml of a 1.04 molar lithium borohydride solution in tetrahydrofuran (2 mmol) and the mixture is stirred at 40°–45° C. for 2 hours. After cooling 3 ml of 3N HCl are added dropwise thereto at 10°–15° C. The mixture obtained is then stirred at 70° C. for 30 minutes and susequently extracted in 2 separating funnels with 100 ml of ether each time. The organic phases are washed four times with 50 ml of water each time, combined, dried over sodium sulphate and concentrated. The residue is chromatographed on 150 g of silica gel with 600 ml of n-hexane/ether (4:6, v/v) and 800 ml of toluene/acetone/glacial acetic acid (92:5:3, v/v). There is obtained (3aS,6aR)-1,3-dibenzyl-dihydro-1H-furo[3,4-d]imidazole-2,4(3H,3aH)-dione with $[\alpha]_D^{20} = +49.3°$ (1% in CHCl₃), which corresponds to an optical purity of 79.5% e.e.

EXAMPLE 5

0.673 g (2 mmol) of cis-1,3-dibenzyl-hexahydro-1H-furo[3,4-d]imidazole-2,4,6-trione and 0.435 g (2 mmol) of (−)-3,3-diphenyl-2-butanol ($[\alpha]_{365}^{20} = -338.9°$ (1% in ethanol)) in 5 ml of toluene are heated under reflux for 6 hours in an apparatus standing under argon. After cooling 0.28 ml (2 mmol) of triethylamine and 5 ml of tetrahydrofuran are added thereto. The solution obtained is added dropwise within 30 minutes at 40° C. under argon to a solution of 4.8 ml of a 1 molar lithium borohydride solution in tetrahydrofuran (4.8 mmol) and the mixture is left to react at 40° C. for 14 hours. The excess hydride is decomposed at 10° C. with 5 ml of 3N HCl and the mixture is stirred at 60° C. for 30 minutes. The product obtained is isolated and purified as described in Example 2 and there is obtained 0.333 g of (3aS,6aR)-1,3-dibenzyl-dihydro-1H-furo[3,4-d]imidazole-2,4(3H,3aH)-dione. $[\alpha]_D^{20} = +38.7°$ (1% in CHCl₃), which corresponds to an optical purity of 62.4% e.e.

EXAMPLE 6

In a manner analogous to Examples 1–5, cis-1,3-dibenzyl-hexahydro-1H-furo[3,4-d]imidazole-2,4,6-trione was reacted with various alcohols and the half ester was reduced. The results are compiled in the following Table.

TABLE

| Alcohol | $[\alpha]_{365}^{20}$ (1% in ethanol) | Lactone of formula I $[\alpha]_D^{20}$ (1% in CHCl₃) | % e.e. |
|---|---|---|---|
| A | +5.0° | +38.0° | 61.3 |
| B | −55.7°** | +45.0° | 72.6 |
|   |   | +51.8°* | 83.5* |
| C | −1.7°** | +45.6° | 73.6 |
| D | −186.8° | +45.9° | 74.0 |
|   |   | +54.5° | 87.9* |
| E | −151.1° | +46.0° | 74.2 |
|   |   | +49.1°* | 79.2* |
| F | +29.1°** | +51.7° | 83.4 |
| G | −212.9° | +52.3° | 84.4 |
|   |   | +55.0°* | 88.7* |
| H | −338.9° | +53.6° | 86.5 |
|   |   | +59.0°* | 95.2* |

*Lactone recrystallized from isopropanol
**$[\alpha]_D^{20}$ instead of $[\alpha]_{365}^{20}$
A = (+)-α-methyl-1-phenylcyclohexanemethanol
B = [S]-(−)-1-(2,4,6-trimethylphenyl)-ethanol
C = (−)-1-(9-anthryl)-ethanol
D = (−)-1-(2,4,6-triethylphenyl)-ethanol
E = (−)-1-(2,4,6-triisopropylphenyl)-ethanol
F = [S]-(+)-1,1,1-triphenyl-2-propanol
G = [S]-(−)-1,1-diphenyl-2-propanol
H = (−)-3,3-diphenyl-2-butanol

We claim:
1. An optically active compound of the formula

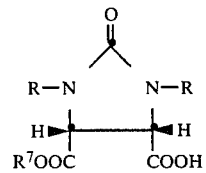

IV wherein R is benzyl; R⁷ is a residue of the formula

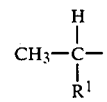

and R¹ is a residue of the formula

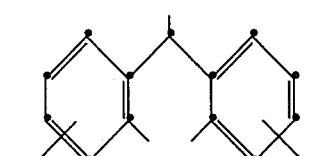

(a)

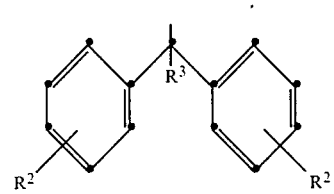

(b)

-continued

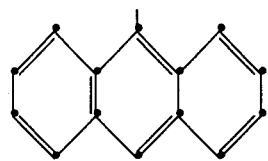
(c)

(d)

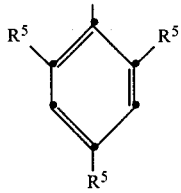
(e)

or

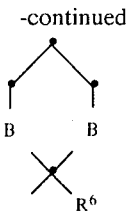
(f)

in which $R^2$ is hydrogen, halogen, lower alkyl or lower alkoxy; $R^3$ is hydrogen or hydroxy or, when $R^2$ in the residue (b) is hydrogen, $R^3$ also can be lower alkyl, lower alkoxy or phenyl; $R^4$ is cycloalkyl selected from the group consisting of cyclopropyl, cyclobutyl, cyclopentyl, cyclohexyl and cycloheptyl, thienyl, 2-furyl or phenyl which phenyl is unsubstituted or substituted with chlorine or methyl; $R^5$ is hydrogen or lower alkyl; $R^6$ is lower alkyl or phenyl; A is sulphur or methylene, B is sulphur, —$SO_2$— or methylene; and n is the integer 1 when A is sulphur or n is the integer 1 or 2 when A is methylene.

2. The compound of claim 1 wherein $R^1$ is the residue of the formula

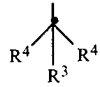
(d)

3. The compound of claim 1, 5-[-[s]-1,1-diphenyl-2-propyl]-cis-1,3-dibenzyl-2-oxo-4,5-imidazolidinedicarboxylate-monoester.

4. The compound of claim 1, 5-[1-(10,11-dihydro-5H-dibenzo[a,d]cyclohepten-5-yl)ethyl]-cis-1,3-dibenzyl-2-oxo-4,5-imidazolidinedicarboxylate-monoester.

* * * * *